United States Patent

Crumpacker et al.

[11] Patent Number: 5,620,645
[45] Date of Patent: Apr. 15, 1997

[54] PROCESS FOR FORMING HIGH TEMPERATURE RESISTANT ELEMENTS

[75] Inventors: Jill E. Crumpacker; Chuong Q. Dam, both of Peoria; Virgil R. Hester, Delavan; Kurtis C. Kelley, Washington, all of Ill.

[73] Assignee: Caterpillar Inc., Peoria, Ill.

[21] Appl. No.: 322,819

[22] Filed: Oct. 13, 1994

[51] Int. Cl.$^6$ .................................................. B29C 71/00
[52] U.S. Cl. .......................................... 264/234; 264/322
[58] Field of Search .................................... 264/234, 322

[56] References Cited

U.S. PATENT DOCUMENTS 3,804,648  4/1974  Birchall et al. .......................... 106/56
5,415,824  5/1995  Barrall et al. ........................... 264/212

FOREIGN PATENT DOCUMENTS 1261282  10/1989  Japan.

Primary Examiner—Christopher A. Fiorilla
Attorney, Agent, or Firm—Pankaj M. Khosla; Frank L. Hart

[57] ABSTRACT

A process for forming elements for use in high temperature environments includes the following steps. The process mixes metal and/or metal compounds with orthophosphoric acid and adds a filler to form a moldable material. The moldable material is dried at a temperature less than about 100 degrees to form a stable unitary mass and thereafter the temperature is increased to its "false melt" temperature. Pressure is then subjected on the element while maintaining the element at its false melt temperature for densifying the element to a preselected porosity and deforming the element to preselected final dimensions.

10 Claims, No Drawings

PROCESS FOR FORMING HIGH TEMPERATURE RESISTANT ELEMENTS

DESCRIPTION

1. Technical Field

The present invention relates to a process for forming high temperature resistant elements. More particularly, the invention relates to a chemical composition utilizing "false melt" processing techniques.

2. Background Art

Amorphous, metal phosphates have been used for dental cements, binding waste into bricks, and high temperature cements and refractory binding agents. An example disclosure of such materials is found in U.S. Pat. No. 3,329,516 "Binding Agent for Refractories and Its Manufacture" which has a priority date of Nov. 15, 1960 and was issued to T.C. Chvatal on Jul. 4, 1967.

The manufacturing processes of these heretofore utilized phosphate materials for forming elements for use in high temperature environments, for example as port liners in the exhaust system of a diesel engine or as adhesive joints in between non-porous materials or low-porosity materials, required undesirable processing time for the removal of water therefrom, undesirable temperature requirements, and undesirable porosity of the resultant element. Such problems represented a waste of time, labor, equipment and natural resources.

The present invention is directed to overcome one or more of the problems as set forth above.

DISCLOSURE OF THE INVENTION

In one aspect of the invention, a process is disclosed for forming elements for use in high temperature environments. In the process, one of a metal, metal compound, and mixtures thereof is mixed with orthophosphoric acid in amounts sufficient to substitute for about 1 to about 2.8 of the three hydrogen ions of orthophosphoric acid. A filler is then added to the mixture for forming a resultant moldable material. The filler is a refractory material and is added in an amount in the range of about 50% to about 95% by weight of the resultant moldable material. Sufficient pressure is exerted on the moldable material to form a molded element of preselected configuration.

The molded element is then dried at a temperature less than about 100 degrees C. for a period of time sufficient to remove water and harden the element to a stable unitary mass. The temperature is thereafter increased to a temperature within the range of the "false melt" temperature of the element to a temperature less than about 300 degrees C. While maintaining the element at a temperature within the "false melt" temperature range, pressure is applied on the element for densifying the element to a preselected porosity and deforming the element to preselected final dimensions.

BEST MODE FOR CARRYING OUT THE INVENTION

In the process of this invention, one of a metal, metal compound, and mixtures thereof is mixed with orthophosphoric acid in an amount sufficient to substitute from 1 to 2.8 of the three hydrogen ions of orthophosphoric acid. Substituting less than one of the three hydrogen ions is undesirable because the phosporic acid is insufficiently neutralized and is free to react with the hereinafter discussed filler. Reaction with the filler results in longer process times and in the liberation of hydrogen gas which undesirably increases the porosity of the element. Substituting greater than about 2.8 of the three hydrogen ions is undesirable because the product is not sufficiently reactive to act as a binder. Excess metal may also remain unreacted and function as a contaminant to the composition of the final product after the filler is added. In some cases, addition of too much metal may result in the crystallizing of the metal phosphate out of solution thereby destroying the binding properties of the mixture. Water acidified to a pH of 1.2 with orthophosphoric acid can also be added to the reacting mixture for maintaining a low viscosity.

A filler is then added to the mixture and a resultant moldable material is formed which has a dough-like consistency. The filler is a refractory material and is added in an amount in the range of about 50% to about 95% by weight of the resultant moldable material.

Filler in an amount less than about 50% is undesirable because it would result in excess binder which interferes with dense particular packing of the filler upon drying and later "false melt" forming and result in excessive shrinkage on drying and undesirable low density of the finished product.

Filler greater than about 95% is undesirable because there is insufficient binder to fully fill the voids in the packed filter and would result in undesirable higher porosity and low strength.

Sufficient pressure is then exerted on the moldable material using methods known in the art of plastic molding and wax or ceramic castings resulting in the formation of an element of preselected configuration that is slightly larger than the dimensions of the desired final element.

The molded element is thereafter dried at a temperature less than about 80 degrees C. for a period of time sufficient to remove water and harden the element to a stable unitary mass. The temperature of the hardened article is rapidly increased to a temperature in the range within the "false melt" temperature of the element of about 180 degrees C. at which the element exhibits visible plastic properties. Temperatures greater than the "false melt" temperature are undesirable because the element will no longer exhibit the plastic behavior and be desirably densifiable.

Therefore, while maintaining the element at a temperature within the "false melt" temperature, pressure is applied on the element for densifying the element to a preselected porosity and deforming the element to preselected final dimensions. It should be understood that by use of the term "false melt" it is meant a change in the material on heating to a specific temperature range where the material temporarily becomes plastic and mimics a melt. Unlike a true melt, which occurs at a much higher temperature and where the composition of the material is unchanged, some material is lost during the "false melt".

It is believed that during the "false melt" sufficient energy has been introduced into the system to release bond and/or tightly held waters that are not removed during lower temperature drying. The metal phosphate binder, still partly hydrated, is momentarily dissolved in the newly released waters and the mixture softens sufficiently to become moldable. Above the "false melt" temperature range, most of the waters are lost from the material and the material hardens to a stable form. The "false melt" is not reversible so the material does not exhibit the same properties again. Because very little water is actually involved, little porosity due to water loss remains.

The metal or metal compound that is utilized in this invention is one of aluminum hydroxide, aluminum, aluminum oxide, iron, nickel, copper, cupric oxide, silica, boron oxide, silver, chromium trioxide, magnesium oxide, zinc oxide and mixtures thereof, preferably a mixture of chromium trioxide and aluminum hydroxide, preferably in the range of about 10% to about 50% by weight chromium trioxide and more preferably where the chromium trioxide is about 27% of said metal compound mixture.

The filler which is added to the metal salt mixture is one of aluminum oxide, silicon nitride, mullite, zirconia and mixtures thereof, preferably aluminum oxide in an amount of about 70% of said moldable material. Other fillers known in the art of plastic molding and ceramic processing, other ceramic and mineral as well as metal powders, platelets and fibers and organic fibers can be used.

In the process, the moldable material is positioned in a die for exerting pressure thereon and forming an element of preselected configuration and the element is dried to a stable unitary mass at a temperature less than about 100 degrees C.

Process examples of high temperature resistant articles are as follows:

EXAMPLE 1

13 gm. of hexavalent chromium oxide is dissolved in 94 ml. of 85% orthophosphoric acid at about 115 degrees C. The mixture is cooled and 160 ml. of water, acidified to a pH of about 1.2 with phosphoric acid, is added. 3 gms. of common table sugar is slowly added and stirred into the mixture reducing the hexavalent chrome to trivalent. Because this reaction is exothermic and can become vigorous, care should be taken to limit the rate of addition of the sugar and allow additional room in the reaction vessel for foaming. 37 gm. of fine grained alumina powder is added and stirred at about 80 degrees C. until the cloudiness of the mixture disappears. An additional 150 ml. of acidified water is added to thin the mixture. 10 gm. of 1200 grit aluminum powder is slowly added and stirred taking the same precautions as in the addition of sugar. The reaction is suitably complete when no further gas is evolved from the mixture and a skin forms over the liquid on exposure to air. Any unreacted solids are centrifuged out and the resultant syrup-like liquid is now referred to as "binder." The binder may be stored in sealed polyethylene containers indefinitely.

A filler is prepared by mixing 65 gm. Alcoa ™ A-16 alumina with 257 gm. Alcoa ™ A-17 alumina. 178 gm. of the prepared binder is blended in with the filler and the resulting mixture wedged with additional filler, by methods well known to those skilled in the art of pottery, to produce a dough with a stiff, workable, clay-like consistency. The dough may be stored in sealed polyethylene bags for at least several weeks.

The dough is placed in a teflon coated ram-type die, suitable for producing a 76.2 mm diameter disk about 25 mm thick. An axial load of about 50 kgs./sq. cm. is applied to the ram to form the dough into a disk and the resulting disk is ejected from the mold.

The disk is placed in a 70 degree C. drying oven for two weeks to remove water. A suitable method of evaluating sufficient water loss is to make periodic weight measurements of the disk and plot the weight vs. time on paper. When the slope of the line indicates a relatively rapid rate of weight loss change (i.e. 3.5 gms./day to 1 gm./day) the disk is ready for "false-melt" forming. Drying times will vary depending on the accuracy of the binder mixture, the amount of water lost from the binder during processing, the dimensions of the part being formed, and oven configuration, etc.

After drying, the disk is very hard and may be handled and stored for at least several weeks without special precautions under normal room conditions.

The disk, which, after drying, is slightly smaller than originally pressed, is heated to about 100 degrees C. at 10 degrees per minute and placed in the original die that has been preheated to 200 degrees C. The die and disk are immediately placed in a hot press preheated to 270 degrees C. and a 50 kg./sq. cm. axial load is applied to the disk. The disk, thus prepared, rapidly heats to within its "false-melt" temperature of about 132 degrees C. to 200 degrees C. and, becoming temporarily plastic, decreases in thickness and reforms to the diametrical dimension of the die. The disk is left in the die, under load, until the "false-melting" range is passed and the disk no longer exhibits plastic behavior, about 5 minutes. Heating the die to 270 degrees C. will aid ejecting the disk from the die due to the thermal expansion differences between a steel die and the phosphate bonded alumina disk, the disk having a lower coefficient of thermal expansion.

The disk, thus formed, has low porosity and a precise diameter controlled by the internal diameter of the die. The disk will withstand temperatures exceeding 1000 degrees C. without significant change in 10 physical properties.

EXAMPLE 2

A bent tube, usable, for instance, as an exhaust port line, is described as follows: A binder is prepared as in Example 1 and mixed with the same proportions of filler but substituting zirconia powder for alumina. An additional 30 gm. of binder and 50 ml. of acidified water is added to the mixture to form a thick slurry. The slurry is poured into and out of a two piece mold, with one opening, whose internal cavity represents a 50 mm dia.×300 mm rod bent at 90 degrees at the middle. The coating of slurry left on the internal mold wall is dried at 95 degrees C. for 15 minutes and the slurry is again poured into and out of the mold. The wall thickness of the tube is thus controlled by the slurry viscosity and the number of times the above steps are repeated. The mold is opened and the tube allowed to dry at 80 degrees C. for 1 hr.

The dried tube is placed back into the mold preheated to 100 degrees C. and the open end of the mold fitted with a silicone balloon. The balloon is charged with 180 degree C. silicone oil to fill the internal cavity of the tube and slowly pressured to about 35 kgs./sq. cm. and held for 5 minutes. The tube softens during "false-melt", densifying, tube against, mold wall. The silicone fluid is withdrawn and the tube removed from the mold. Additional heat, up to 1300 degrees C., may be used to remove any residue of water prior to putting the tube into service.

EXAMPLE 3

A high-temperature, check-valve can be manufactured in the following manner: An iron-chromium-phosphate binder is prepared by dissolving 26.2 gm. iron powder in 110 ml. of 85% orthophosphoric acid. A white precipitate forms and settles. 100 ml. of acidified water and 41 gm. of chromium trioxide are added and the solution heated to about 90 degrees C. and continuously stirred until the precipitate dissolves. 9 gm. of sugar are added using precautions detailed in Example 1 and additional acidified water is added to maintain a low enough viscosity to allow bubbles to break. The binder, thus formed, can be stored in polyethylene containers when all signs of reaction have ended.

50 gm. of alumina filler, as described in Example 1, is mixed with 5 gm. carbon fiber. This mixture is combined with about 40 gm. of the binder to form a soft, clay-like material. The material is then injection molded into a three part mold consisting of: 1. a two piece mold whose internal cavity represents the exterior dimensions of the finished check valve and, 2. a one piece insert which represents the internal check-valve dimensions. The insert is further composed of lead into which a spring and ball have been cast.

After molding the binder-filler mixture, the exterior mold is removed and the piece dried at room temperature for 8 hours. The piece is isostatically pressed at 10 kgs./sq. cm. and 150 degrees C., which is within the false melt temperature range of material so prepared, to densify the piece against the insert. The piece remains under the load and temperature for 10 minutes and removed. Dipping the piece in molten lead melts out the lead insert, leaving the ball and spring check valve components in place. A fiber-reinforced check valve is so formed with a complex internal cavity, suitable for high temperature use, without machining or seams.

EXAMPLE 4

A mixture of binder and filler may be dried and ground into a powder and reformed under pressure in the "false-melt" temperature range. The phosphate binder and alumina dough described in Example 1 is dried at room temperature for about 1 week or until grindable into a powder. The material is put through a grinding mill and reduced to a powder of about 50 micron size.

About 20 gm. of powder is placed in a 25 diameter die, preheated to 250 degrees C., and immediately pressed into a disk under a 1000 kgs./sq. cm. load. Sufficient heat is transferred from the die to elevate the lower temperature to its "false-melt range." The load is maintained on the powder for about 5 minutes after which the resulting phosphate-bonded alumina pellet is ejected from the die. The hard, dense pellet is 25 mm. dia.× about 12 mm. thick and after heating to about 250 degrees C., to ensure more complete removal of water, is suitable as a sharpening stone for small laboratory blades.

EXAMPLE 5

A temperature-sensitive adhesive sheet, suitable for bonding flat steel surfaces can be prepared from a metal-phosphate binder and filler. The dough, described in Example 1, can be rolled through a pasta machine to form a sheet about 1 mm thick. The sheet can be cut with cookie-type cutters to any desired dimensions and dried on a flat surface for 10 min. at 90 degrees C. These adhesive sheets may be stored at room temperature for, at least, several weeks.

When placed between two flat steel plates, preheated to 200 degrees C., and the contact area immediately loaded to 1000 kgs./sq. cm., the phosphate-filter sheet conforms to and bonds with the steel plates as the sheet temperature rises to within the "false-melt" temperature range. The adhesive joint, thus formed, will withstand high temperatures and, on ultimate-strength testing, exhibits cohesive failure within the adhesive without adhesive failure from the steel plates.

EXAMPLE 6

A high temperature, functionally-gradient bond may be made between steel and ceramic during "false-melt" processing by layering dried adhesive sheets of varying compositions, similar to those described in Example 5. Bonding ceramics to metal for high temperature applications is extremely difficult due to both the large thermal properties mismatch between the two materials and the lack of adhesives capable of temperatures over 300 degrees C. The thermal and mechanical properties of the phosphate materials, described in the above examples, are largely controlled by the fillers used. By grading a joint from a high thermal-expansion, high thermal-conduction material adjacent to the metal surface to a low thermal-expansion, low thermal-conduction material adjacent to the ceramic surface, a bond can be formed that resists failure due to thermal cycling.

Five thick binder-filler slurries are first prepared as follows: Slurry 1 is prepared by combining 80 gm. of copper powder, 8 gm. A-16 alumina, and 32 gm A-17 alumina with 50 gm. of the chromium-aluminum-phosphate binder described in Example 1. Slurry 5 is prepared by combining 20 gm. A-16 alumina and 80 gm. A-17 alumina with 70 gm. of the same binder. Slurries 2, 3, and 4 are prepared by mixing 75/25, 50/50, and 25/75 proportions of Slurries 1 and 2, respectively.

Slurry 1 is tape cast into a thin sheet onto acetate using a doctor's blade, set at 0.2 mm, by methods well known to the art of ceramic processing. After drying the tape for about 20 minutes, at room temperature, Slurry 2 is tape cast directly over the first tape by raising the doctor's blade an additional 0.2 mm. Each successive slurry is cast in the same manner, allowing the drying time between each casting. In this way, an approximately 1.0 mm thick tape is produced which grades, through its thickness, from a high copper content to a high alumina content. The tape is dried at room temperature for 16 hours.

The tape, thus formed, is placed between a steel and an alumina plate which have been preheated to 200 degrees C. and are mounted on heated platens in a hydraulic press, making sure the high copper side of the tape is adjacent to the steel, and immediately pressed at about 10 kgs./sq. cm. The tape becomes plastic as it enters the "false-melt" temperature range and considerable densification takes place under the load and the binder also reacts and bonds to the plates. The load and heat are maintained for about 5 minutes and the steel bonded to alumina part is removed.

EXAMPLE 7

1. Thin coating of unfilled metal-phosphate applied to component surface.
2. Coating dried.
3. Component pressed onto hot mating surface causes "false-melt" of phosphate and bond.

We claim:

1. A process for forming elements for use in high temperature environments, comprising:

mixing one of a metal, metal compound, and mixtures thereof having water of hydration, with orthophosphoric acid, said orthophosphoric acid having three hydrogen ions, in an amount sufficient to substitute about 1 to about 2.8 of said three hydrogen ions of orthophosphoric acid;

adding a filler to the mixture and forming a resultant moldable material, said filler being a refractory material and being added in an amount in a range of about 50% to about 95% by weight;

exerting sufficient pressure on said moldable material to form a molded element;

drying the molded element at a temperature less than about 100 degrees C. for a period of time sufficient to harden the element to a stable unitary mass;

increasing the temperature of the element to within the range of its temperature of "false melt"; and applying pressure on the element, while maintaining the element within the range of its "false melt" temperature, removing a portion of said water of hydration and densifying the element and deforming the element to final dimensions.

2. A process, as set forth in claim 1, wherein said metal compound is one of aluminum hydroxide, chromium trioxide, magnesium oxide, zinc oxide and mixtures thereof.

3. A process, as set forth in claim 2, wherein said metal compound is a mixture of chromium trioxide and aluminum hydroxide.

4. A process, as set forth in claim 3, wherein said chromium trioxide of said metal compound is in a range of about 10% to about 50% by weight of said metal compound.

5. A process, as set forth in claim 4, wherein Said chromium trioxide of said metal compound is about 27% by weight of said metal compound.

6. A process, as set forth in claim 1, wherein said filler is one of aluminum hydroxide, silicon nitride, mullite, zirconia, and mixtures thereof.

7. A process, as set forth in claim 6, wherein said filler is aluminum oxide.

8. A process, as set forth in claim 1, wherein said metal, metal compound and mixtures thereof are in an amount sufficient to substitute about 1.9 of said three hydrogen ions of orthophosphoric acid.

9. A process, as set forth in claim 1, including positioning the resultant moldable material in a die for exerting pressure thereon and forming an element.

10. A process, as set forth in claim 1, wherein said element is dried into a stable unitary mass at a temperature less than about 70 degrees C.

* * * * *